(12) United States Patent (10) Patent No.: US 7,560,286 B2
Naoki et al. (45) Date of Patent: Jul. 14, 2009

(54) MASS SPECTROMETRIC METHOD FOR STRUCTURAL ANALYSIS OF CHAIN NITROGEN-CONTAINING COMPOUNDS USING SQAURIC ACID

(75) Inventors: Hideo Naoki, Sakai (JP); Terumi Nakajima, Shinjuku-ku (JP); Yasufumi Ohfune, Takatsuki (JP); Tetsuro Shinada, Sakai (JP); Kazuya Murata, Otokuni-gun (JP)

(73) Assignee: Suntory Holdings Limited, Osaka-shi (JP)

( * ) Notice: Subject to any disclaimer, the term of this patent is extended or adjusted under 35 U.S.C. 154(b) by 1040 days.

(21) Appl. No.: 10/095,017

(22) Filed: Mar. 12, 2002

(65) Prior Publication Data

US 2004/0067525 A1 Apr. 8, 2004

(30) Foreign Application Priority Data

Aug. 10, 2001 (JP) ............................. 2001-244653

(51) Int. Cl.
*G01N 24/00* (2006.01)
(52) U.S. Cl. ....................................... 436/173; 436/106
(58) Field of Classification Search .................. 436/40, 436/173
See application file for complete search history.

(56) References Cited

U.S. PATENT DOCUMENTS

| 5,004,661 | A | * | 4/1991 | Law et al. | .................. | 430/58.8 |
| 5,145,774 | A | * | 9/1992 | Tarnowski et al. | ......... | 435/7.25 |
| 5,278,031 | A | * | 1/1994 | Boggs et al. | ................ | 430/348 |

OTHER PUBLICATIONS

Shinada, et al., "Efficient Synthesis of a Novel 4-Hydroxyl-2,3-dioxocyclobut-1-enyl Group Containing Amino Acids," Organic Letters (1999) vol. 1(10, pp. 1663-1666.*

Tetsuro Shinada, et al., "Efficient Synthesis of a Novel 4-Hydroxy-2,3-dioxocyclobut-1-enyl Group Containing Amino Acids" Organic Letters, vol. 1, No. 10, 1999, pp. 1663-1666.

Changfu Cheng, et al., "Applications and Mechanisms of Charge-Remote Fragmentation" Department of Chemistry, Washington University, Oct. 17, 2000.

"Abstracts of Lectures II" The Chemical Society of Japan, 79th Spring Annual Meeting of the Chemistry Society of Japan 2001 with English Translation.

* cited by examiner

*Primary Examiner*—Yelena G Gakh
(74) *Attorney, Agent, or Firm*—Crowell & Moring LLP (57) ABSTRACT

A method for effectively causing charge-remote fragmentation (CRF) when the structural analysis of an nitrogen-containing organic compound is performed using a high-energy collisional-induced dissociation-mass/mass spectrum (CID-MS/MS spectrum), a reagent to be used in such a method, and a method for analyzing an organic compound by the induction of CRF are provided. The method for the induction of charge-remote fragmentation (CRF) using a high-energy collisional-induced dissociation-mass/mass spectrum (CID-MS/MS spectrum) has the step of: introducing a squaric acid residue into an end of a nitrogen-containing organic compound. The squaric acid residue is represented by a chemical formula (I):

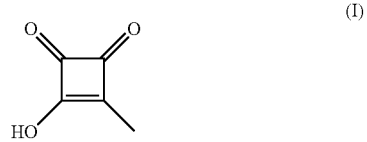

The reagent is provided for introducing such a squaric acid residue. Furthermore, the method is provided for analyzing such an organic compound by the induction of CRF.

3 Claims, 4 Drawing Sheets

MASS SPECTROMETRIC METHOD FOR STRUCTURAL ANALYSIS OF CHAIN NITROGEN-CONTAINING COMPOUNDS USING SQAURIC ACID

BACKGROUND OF THE INVENTION

1. Field of the Invention

The present invention relates to a method for structural analysis of an organic compound using a high-energy collisional-induced dissociation-mass/mass spectrum (hereinafter, simply referred to as CID-MS/MS spectrum). Especially, the present invention relates to a method for causing a charge-remote fragmentation with respect to a nitrogen-containing organic compound and a reagent to be used in such a method.

2. Description of the Background Art

Various kinds of physical and chemical methods have been applied as means for structural analysis and identification of organic materials with unknown or presumptive chemical formulas. In a most commonly accepted way in the prior art, for example, a target organic compound is subjected to the analysis using an infrared absorption spectrum (IR spectrum), a proton- or carbon-nuclear magnetic resonance spectrum ($H^1$- or $C^{13}$-NMR spectrum), a mass spectrum (MS spectrum), an X-ray crystal diffraction or the like, followed by the analysis of the resulting data to determine or identify a chemical formula of the target organic compound, and so on.

These means for structural analysis of organic compounds have been remarkably developed together with scientific and technological advances. For example, a MS/MS method is becoming one of the methods frequently used for advanced structural determination of peptides as nitrogen-containing organic compounds. In general, such a MS/MS method is a combination of an ionization method such as electrospray ionization (ESI) and matrix-assisted laser desorption/ionization with a method of collisional-induced dissociation (CID) that permits molecular dissociation with low energy or post-source decay (PSD).

A MS/MS spectrum to be used in the MS/MS method has several advantages because it is highly sensitive and is measurable in a mixture. Therefore, the MS/MS method is widely used as a method for determining a primary sequence of peptide. In many cases, however, observed sequence ions (dissociated ions) complicate the structural analysis of a target compound. In the case of peptides, for example, the structural analysis can be complicated by the presence of undesired ion peaks generated in a variety of cleavage fashion that usually accompanies with bond-cleavage between carbon-hetero atom bonds. As other advantages, the MS/MS method is capable of obtaining information about the differences in molecular weights corresponding to amino acid residues that make up the target peptide. However, for example, the MS/MS method is difficult to distinguish leucine (Leu) and isoleucine (Ile), which are isomers with respect to each other. In addition, the MS/MS method is also difficult to distinguish glutamine (Gln) and lysine (Lys) which are of the same molecular weight.

For arginine (Arg)- or lysine (Lys)-rich peptides, other basic groups, specifically guanidine groups or amino groups may be also included in their amino acid structures. Thus, the MS/MS method further complicates the structural analysis because of causing a complicated spectrum as a result of dispersing charge sites.

Recently, for solving the above disadvantages, attention is being given to the MS/MS analysis that utilizes charge-remote fragmentation (CRF) to be obtained from high-energy collisional-induced dissociation (CID).

More specifically, the CRF is characterized in that CRF can be observed by performing a molecular ionization using a first-stage mass spectrometer (MS) by introducing a sulfonic acid residue on the molecular end of peptides, especially on N-terminal thereof, or by holding (charging) a polar functional group such as a quaternary ammonium salt residue on the N-terminal, followed by performing forcible fragmentation, i.e., high-energy collisional-induced dissociation (CID).

The CRF observed here is characterized in that unidirectional bond cleavage between not only carbon-hetero atom bonds but also carbon-carbon bonds. Moreover, the CRF occurs from a distant place of a sulfonic acid group or a polar functional group such as a quaternary ammonium salt, which exists on the molecular end, and fragmentation arises regularly in the direction perpendicular to a molecular axis.

Here, the basic fashion of dissociation in which the CRF can be observed will be explained with reference to the following schematic formula. In this schematic formula, each of lower-case letters of the alphabet, a, b, c, d, e, and f, represents each dissociation site of the molecule. These dissociations occur in alphabetical order, i.e., in order of decreasing the distance from the polar function group. Therefore, peaks of product ions that correspond to these dissociations can be specifically observed.

Polar function group

Dissociation form on the basis of CID-MS/MS

The MS/MS method is capable of obtaining structural information of the target compound with high accuracy, compared with the above fragmentation at low energy in which fragmentations from both ends of the target molecule can be observed. Therefore, the CID-MS/MS method exerts its greatest force on the structural microanalysis of organic long-chain compounds such as polyamines and polyether organic molecules, notably brevetoxin.

For applying such a structural analysis on the analysis of peptide structure, there is a need for performing the selective introduction of a polar functional group such as a sulfonic acid residue into the N-terminal of peptide. Alternatively, there is a need of the conversion of such an N-terminal into a quaternary ammonium salt residue or the like. However, some of peptides, e.g., mastoparan, bradykinin, insurin, etc., involve the basic amino acid residues on their side chains that may be arginine (Arg), lysine (Lys), ornithine, and diaminopropionic acid. Therefore, it is difficult for the person skilled in the art to perform selective sulfonation only on the N-terminal of each of these compounds or to convert such an N-terminal into a quaternary ammonium form.

SUMMARY OF THE INVENTION

In view of the above disadvantages of the prior art, the object of the present invention is to provide: a method for effectively causing charge-remote fragmentation (CRF) when the structural analysis of a nitrogen-containing organic compound is performed using a high-energy collision-induced dissociation (CID)-MS/MS spectrum; a reagent to be used in such a method; and a method for structural analysis of an organic compound by the induction of CRF.

For solving the above disadvantages, the present invention provides a method for inducing charge-remote fragmentation (CRF) by means of a high-energy collision-induced dissociation (CID)-MS/MS spectrum, comprising the step of introducing a squaric acid residue into an end of a nitrogen-containing organic compound, where the squaric acid residue is represented by the formula (I):

That is, the present invention essentially requires the presence of strong acidic or strong basic polar function group on the end of a long-chain molecule for the induction of regular CRF using CID-MS/MS spectrum. Therefore, the present invention is characterized by using a squaric acid residue represented by the formula (I) as such a polar function group. The squaric acid has both strong acidity and aromaticity.

According to the studies conducted by the present inventors, squaric acid provided as a main part of the squaric acid residue represented by the above formula (I) has a strong acidity substantially equal to that of trifluoroacetic acid which has intermediate acidity between the sulfuric acid and the organic carboxylic acid. In addition, the induction of regular CRF can be observed by the CID-MS/MS method with the introduction of a squaric acid residue into the end of nitrogen-containing organic compound (i.e., squarylation). The present inventors are the first to have the application of CRF induction by introducing a squaric acid residue into the end of nitrogen-containing organic compound. In other words, it has not been disclosed or taught in any publications before the present invention.

Therefore, the present invention provides a reagent as another embodiment for introducing a squaric acid residue into an end of a nitrogen-containing organic compound for inducing charge-remote fragmentation (CRF) by means of a high-energy collision-induced dissociation (CID)-MS/MS spectrum, where the squaric acid is represented by the formula (I):

According to the invention provided by claim 4, the specific reagent for introducing the squaric acid residue may be a squaric acid derivative represented by the formula (II):

wherein each of $R^1$ and $R^2$ similarly or differently represents a hydrogen atom, a lower alkyl group, an alkenyl group, an aryl group, or an aralkyl group.

For example, in the case of a nitrogen-containing organic compound having an amino group on its molecular end, the squaric acid residue represented by the formula (I) can be effectively introduced into the amino group of the molecular end using the squaric acid derivative represented by the formula (II) to directly react the organic compound with such a derivative.

Also, as means for introducing the squaric acid residue represented by the formula (I) into the end of the nitrogen-containing organic compound, a compound having a squaric acid residue may be coupled to that end using appropriate procedures only of synthetic organic chemistry. This described where the reagent for introducing the squaric acid residue may be a squaryl amino acid derivative represented by the formula (III):

wherein $R^3$ represents a hydrogen atom, a lower alkyl group, an alkenyl group, an aryl group, or an aralkyl group, $R^4$ represents a protecting group for an amino group, and n denotes a positive integer 1 or 2.

Furthermore, the present invention provides a method for structural analysis of an organic compound using the induction of regular CRF by means of CID-MS/MS spectrum wherein the method comprises the steps of introducing a squaric acid residue into a molecular end of a nitrogen-containing organic compound, where the squaric acid is represented by the formula (I):

and inducing CRF in the nitrogen-containing organic compound using CID-MS/MS.

For the induction of regular CRF using CID-MS/MS, in other words, the above method is characterized in that the squaric acid residue having the formula (I) is introduced into the molecular end of the nitrogen-containing organic compound to be provided as a target of the structural analysis.

A method for the introduction of squaric acid residue having the formula (I) may comprise of the step of directly introducing the squaric acid residue into the molecular end of the target nitrogen-containing organic compound, or organic-chemically bonding a compound having a squaric acid residue to the molecular end of the target nitrogen-containing organic compound.

Therefore, as another aspect of the above invention, there is provided a method for introducing a squaric acid reside on an end of an organic compound in a method for structural analysis of such an organic compound. More concretely, the invention provides a method for structural analysis of an organic compound which may include the step of using the squaric acid derivative represented by the formula (II) for introducing a squaric acid residue into the molecular end of the nitrogen-containing organic compound.

Furthermore, the invention provides a method for structural analysis of an organic compound which may include the step of using a squaryl amino acid derivative represented by the formula (III) for introducing a squaric acid residue into the molecular end of the nitrogen-containing organic compound.

DETAILED DESCRIPTION OF THE PREFERRED EMBODIMENTS

Organic compounds to be used in the present invention for structural analysis of a nitrogen-containing organic compound where the induction of CRF is performed using CID-MS/MS, may be any compounds having amino groups on their molecular ends. Such compounds may include: those having structures analogous to amino acids; peptides; peptide esters; polyamines; polyamine ethers; organic chain compounds having amino groups on their molecular ends; and organic cyclic compounds having amino groups on their molecular ends.

These compounds may be natural compounds having unknown structures or compounds having already-determined or presumed chemical formulas. Furthermore, each of these compounds may be one without essentially having a terminal amino group in its molecule as an organic compound or may be one in which the introduction and conversion of an amino group can be performed at the end of its molecule by means of chemical synthesis. In brief, the method or reagent of the present invention can be applied on a compound having a terminal amino group that allows the induction of CRF using CID-MS/MS and thus the chemical formula of such a compound can be determined by identifying the resulting CRF.

Furthermore, the nitrogen-containing organic compounds which can be used in the present invention may include compounds having nucleophilic groups such as guanidines, aromatic and aliphatic alcohols, thiols, indoles, imidazoles, and amines in thier molecules in addition to terminal amino groups. The introduction of squaric acid residue does not react with such functional groups. It is only performed on the terminal amino acid group.

The introduction of squaric acid residue represented by the above formula (I) to be used in the present invention can be mainly performed by one of the following two methods. As a first method, the squaric acid derivative of the above formula (II) is reacted with a nitrogen-containing organic compound for the direct introduction of squaric acid residue. For example, in the case of a nitrogen-containing organic compound having no amino group on its side chain, the introduction of squaric acid derivative having the formula (II) can be directly performed on such a compound under weak-base conditions. Therefore, the introduction of desired squaric acid residue can be attained.

Furthermore, when a compound having a side-chain amino group such as lysine, ornithin, diaminopropionic acid or the like is present in addition to a terminal amino group, the selective introduction of squaric acid residue into the terminal amino group can be performed by the steps of protecting the above amino groups with the conversion to phenylthiourea form or the like (e.g., lysine is converted to thiocarbamate form) by the Edman degradation method or the method in combination with a new Edman degradation method developed by the present inventors based on the Edman degradation method, followed by reacting with a squaric acid derivative.

As a second method, for example, a compound having a squaric acid residue is chemically coupled to a nitrogen-containing organic compound substantially to introduce the desired squaric acid residue into a molecular end of the nitrogen-containing organic compound. More specifically, a nitrogen-containing organic compound can be converted into one having a squaric acid reside of the formula (I) on its molecular terminal by the use of the squaryl amino acid derivative of the formula (III) in an organic chemical manner.

The second method can be applied on a compound having a substituent to be chemically coupled to the squaryl amino acid derivative having the formula (III) on its molecular end. Such a substituent may be an amino group, a hydroxy group, a halogen atom, a carboxyl group, or the like. In the case of peptides, peptide esters, polyamines, and polyamine ethers, which include amino groups in their molecular ends, it is possible to apply the second method on the introduction of squaric acid residue instead of the direct introduction of the squaric acid residue by the above first method using the squaric acid derivative of the formula (II). In this case, the second method may be effective.

For effective induction of CRF using CID-MS/MS, therefore, the present invention also provides a reagent for the introduction of squaric acid residue represented by the above formula (I) into the terminal amino group of a nitrogen-containing organic compound. The reagent may comprise a squaric acid derivative represented by the above formula (II) or a squaryl amino acid derivative represented by the above formula (III).

The reaction conditions for the introduction of squaric acid residue in which the squaric acid derivative of the formula (II) as the reagent of the present invention include specifically, for example, the usage of an appropriate solvent having a pH of about 7 to 8 in which a nitrogen-containing organic compound as a target of the introduction of squaric acid residue can be reacted with the reagent that comprises the squaric acid derivative of the formula (II) to effectively introduce the squaric acid residue into the terminal amino group of the above organic compound.

The above solvent used for the reaction with the squaric acid derivative of the formula (II) to be provided as a regent of the present invention may be any solvents known in the art that do not cause a direct influence on the desired reaction. Specifically, such a solvent may be selected from water, buffers, organic solvents, and mixtures thereof. Preferably, the above organic solvents may be ether-based solvents such as dioxane and tetrahydrofuran. Also, the buffer solutions may be any buffers having pH of about 7 to 8, such as phosphate buffer solutions.

In this case, furthermore, it is found that the selective conversion of amino group to squaryl form can be only performed by adjusting the reaction conditions in various ways. For example, bradykinin includes not only a guanidine group as an amino group on its N-terminal but also another guanidine group as an amino group on its C-terminal. However, the introduction of squaric acid residue cannot be performed on the C-terminal at all by appropriately adjusting the reaction pH.

Therefore, the reagent of the present invention has an excellent utility for the effective induction of CRF using CID-MS/MS. The reagent of the present invention comprises the squaric acid derivative represented by the formula (II) for the squarylation of the terminal amino group of a nitrogen-containing organic compound.

In this case, lower alkyl groups which can be provided as the substituents "$R^1$" and "$R^2$" in the formula (II) for the squaric acid derivative may be straight- or branched-chain alkyl groups having about 1 to 5 carbons. Specifically, the lower alkyl groups may be preferably selected from methyl, ethyl, n-propyl, iso-propyl, n-butyl, sec-butyl, tert-butyl, pentyl, and other groups. Among them, in particular, a methyl group or a tert-butyl group may be preferably used as the above alkyl group.

Also, alkenyl groups which can be provided as the substituents "$R^1$" and "$R^2$" in the formula (II) may include allyl, propenyl and other groups. On the other hand, the aryl group as each of such substituents "$R^1$" and "$R^2$" may be a substituted or unsubstituted phenyl group such as a phenyl group, a toluyl group, a halogenophenyl group, and a nitrophenyl group. Furthermore, the aralkyl group as each of such substituents "$R^1$" and "$R^2$" may be a benzyl group, a phenethyl group, or the like.

The above substituents "$R^1$" and "$R^2$" may be the same or may be different from each other. Among any possible combinations for the substituents "$R^1$" and "$R^2$", the combination of methyl groups or tert-butyl groups may be particularly preferable.

Among the squaric acid derivatives which can be represented by the formula (II) of the present invention, any compounds having methyl groups as both substituents "$R^1$" and "$R^2$" can be commercially available. Thus, such compounds can be used as starting substances for preparing the squaric acid derivatives having other substituents.

As an alternative method, for example, squaric acid derivatives can be prepared according to the method described in *Synthetic Communication:* 27 (12), 2177-2180.

On the other hand, in the case of the introduction of squaric acid residue using the squaryl amino acid derivative of the formula (III) provided as another reagent of the present invention, appropriate means for organic chemical synthesis can be used. For example, a general peptide-synthesis method is applied on a nitrogen-containing organic compound having an amino group on its molecular end. Such an organic compound is reacted with a squaryl amino acid derivative represented by the formula (III), followed by removing a protecting group or the like if it is present, to obtain a target compound having the introduced squaric acid residue.

In this case, lower alkyl groups which can be provided as the substituent "$R^3$" in the formula (III) for the squaryl amino acid derivative may be straight- or branched-chain alkyl groups having about 1 to 5 carbons. Specifically, the lower alkyl groups may be preferably selected from methyl, ethyl, n-propyl, iso-propyl, n-butyl, sec-butyl, tert-butyl, pentyl, and other groups. Among them, in particular, a methyl group or a tert-butyl group may be preferably used as the lower alkyl group.

Also, alkenyl groups which can be provided as the substituents "$R^3$" in the formula (III) may include allyl, propenyl, and other groups. On the other hand, the aryl group as such a substituent "$R^3$" may be a substituted or unsubstituted phenyl group such as a phenyl group, a toluyl group, a halogenophenyl group, and a nitrophenyl group. Furthermore, the aralkyl group as such a substituent "$R^3$" may be a benzyl group, a phenethyl group, or the like.

The protecting group for protecting the amino group of the substituent "$R^4$" means a protecting group for protecting an amino group which is generally used in the art. Specifically, the protecting group may be an acyl group, a benzyl group, an alkoxycarbonyl group, an alkyl sulfonyl group, an arylsulfonyl group, or the like. Specifically, the acyl group may be a lower fatty acid residue such as an acetyl group, a trifluoroacetyl group, and a propionyl group, or a substituted- or unsubstituted-benzoyl group, or the like. The alkoxycarbonyl group may be a t-butoxycarbonyl group (Boc), alkylsulfonyl group may be a methansulfonyl group, and arylsulfonyl group may be a toluenesulfonyl group, a p-toluenesulfonyl group, or the like.

Furthermore, for example, these squaryl amino acid derivatives can be prepared using the method described in *Organic Letters:* 1 (10), 1663-1666 (1999).

As described above, furthermore, if there is lysine in a peptide molecule, which is one having a side-chain amino group, then there are two or more charge sites in the peptide molecule to be squarylated. Therefore, prior to the reaction with the reagent of the present invention, CRF can be effectively caused, in combination with the Edman degradation method, by the utilization of means for protecting the side-chain amino group of lysine by converting it to phenylthiocarbamic form, while removing a terminal amino acid from the peptide molecule by cleavage to convert a free amino group of the second amino acid to squaric form.

That is, if there is lysine in the peptide molecule, an amino group on the side chain of lysine is protected by converting such an amino group to phenylthiocarbamic form using phenylisothiocyanate. On the other hand, an amino group of the terminal amino acid is also converted to phenylthiocarbamic form by a coupling reaction with phenylisothiocyanate. Subsequently, the terminal amino acid converted to phenylthiocarbamic form is subjected to cyclization and break reactions to remove such a terminal amino acid as phenylthiohydantoin from the peptide molecule. As a result, the second amino acid in the original peptide bonds becomes an N-terminal amino acid, whereas the phenyltiocarbaminated amino group on the side chain of lysine is still protected.

In this stage, only a new N-terminal amino group is provided as a charge site to be squarylated. Therefore, CRF can be effectively caused by the reaction with the reagent of the present invention at that stage because of selective squarylation of such an amino group.

In the traditional Edman degradation method, for example, a coupling reaction is conducted using phenylisothiocyanate. If the traditional Edman degradation method is performed, the side-chain amino group of lysine in the peptide molecule is generally converted to phenylthiocarbamine form. However, in the case of another compound having a lot of side-chain amino groups, the conversion of amino group to phenylthiocarbamine form leads to a high lipophilicity, resulting in poor ionization efficiency. Under such conditions, it is found that the desired regular fragmentation can be observed without substantial effectiveness even though the induction of CRF by the squarylation of the terminal amino groups.

Therefore, the present inventors carried out an improved Edman degradation method (i.e., new Edman degradation method) using a compound having the following formula (IV) instead of phenylisothiocyanate used in the traditional Edman degradation method. That is, such a compound is a modified phenylisothiocyanate having a polar substitute on a para position of phenyl group represented by the formula (IV):

(IV)

wherein $R^5$ denotes a substitute having a high polarity. Consequently, the terminal amino acid is removed from the compound by cyclization and break reactions by treating with trifuloroacetic acid. As a result, the second amino acid in the original peptide bonds becomes an N-terminal amino acid, while the amino group on the side chain of lysine is in p-substituted phenylthiocarbamine form by the above compound of the formula (IV). Thus, it is found that CRF can be more effectively caused as the polarity of the substitute on the para-position leads to a high ionization rate.

The substituents for "$R^5$" may include a guanidyl group, a guanidinomethyl group, an amidino group, an amidiomethyl group, and so on. Among them, phenylisothiocyanate having a guanidionomethyl group at a para position of phenyl group allows the preferable results. Consequently, the present invention provides the novel Edman degradation method for peptide compounds comprising lysine and so on.

EXAMPLES

Hereinafter, the present invention will be described in detail with explanations of individual examples. However, the scope of the present invention is not limited to these examples. It should be noted that various modifications and changes of these examples will be within the scope of the present invention.

Example 1

The Preparation of a Squarylating Reagent [i.e., the Synthesis of a Reagent Represented by the Formula (II) in Which $R^1$ Represents a Methyl Group and $R^2$ Represents a Tert-Butyl Group]

Tetrahydrofuran solution of dimethylsquaric ester (3.0 g, 21.1 mmol) (50 ml) was cooled to 0° C. and tetrahydrofuran solution of potassium tert-butoxide(2.4 g, 21.4 mmol) (20 ml) was then dropped while stirring. After 15 minutes, the reaction solution was acidified with the addition of an aqueous solution of 1N hydrochloric acid (HCl), and extracted with diethyl ether. Then, extract was washed and dried. Subsequently, the extract was purified with a silica-gel column chromatography (eluting solvent: hexane/ethyl acetate=5:1), resulting in 1.5 g of a crystallized white product (yield: 39%) as a target compound

Likewise, the following reagents were prepared.

| $R^1$ | $R^2$ |
|---|---|
| $CH_3$ | $CH_3$ |
| $C_2H_5$ | $C_2H_5$ |
| $(CH_3)_2CH$ | $(CH_3)_2CH$ |
| $n-C_4H_9$ | $n-C_4H_9$ |
| tert-Bu | tert-Bu |

Example 2

Squarylation of Angiotensin I and CID-MS/MS Analysis Thereof (3)

500 nmol of tert-butyl methylsquaric ester (2) in dioxane (50 μl) obtained in Example 1 was added in 50 nmol of angiotensin I (1) in 200 μl of phosphate buffer (pH 8) and the resulting mixture was stirred for 2 days at a room temperature. Then, the reaction solution was purified with a high performance liquid chromatography (HPLC), resulting in angiotensin I with squarylated N-terminal as a primary product. As a secondary product, a compound with remaining tert-butyl group deemed to be hydrated was recognized from MALDI/MS spectrum.

The resulting angiotensin I (3) with squarylated N-terminal was subjected to CID-MS/MS analysis. Product ion peaks obtained from such an analysis are shown in a chart diagram of FIG. 1.

Figure 1:
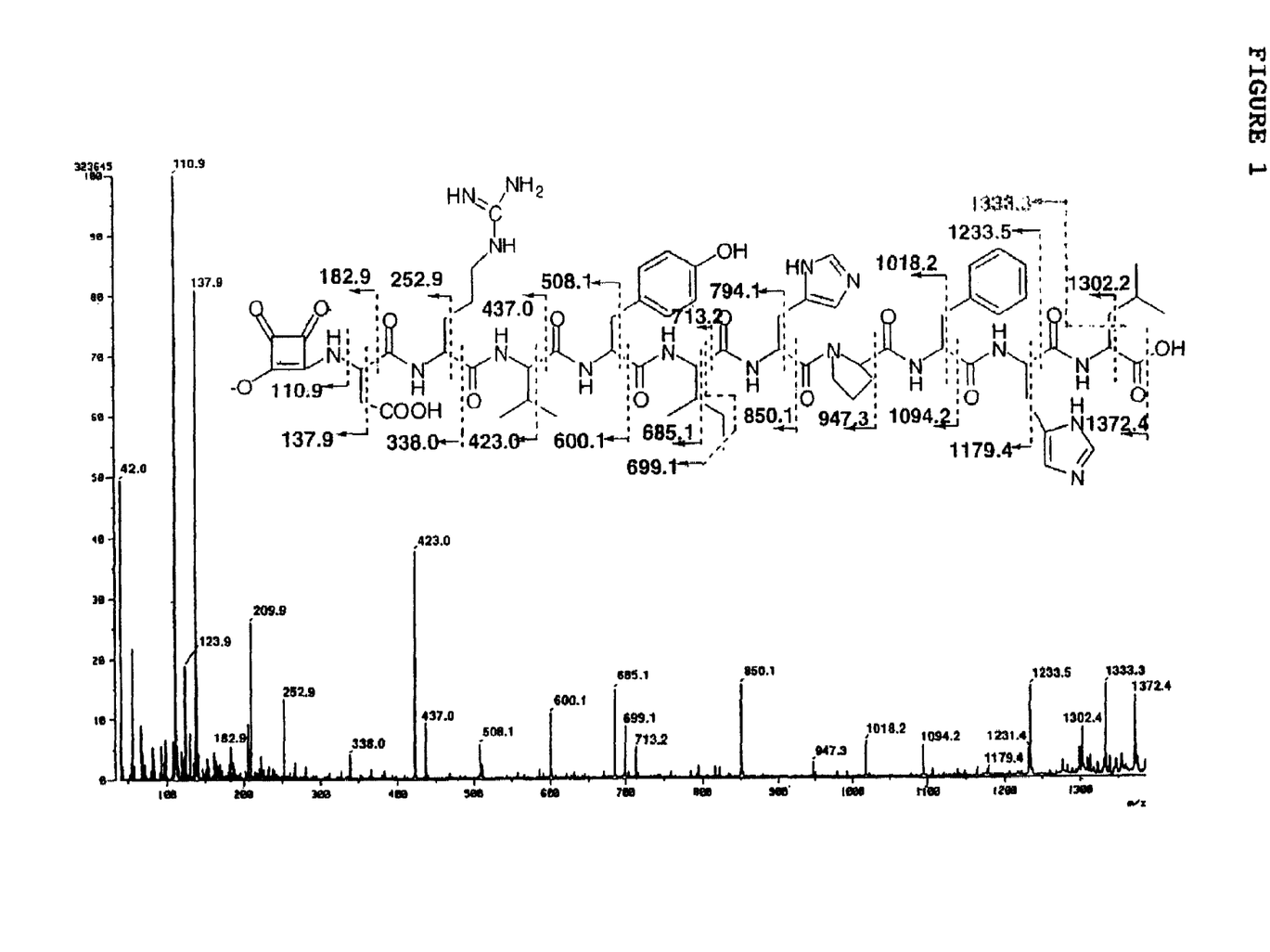
FIG. 1 is a CRF-chart diagram obtained by the CID-MS/MS analysis of squarylated angiotensin-I in Example 2.

As is evident from the chart diagram, the generation of regular CRF is observed.

Example 3

Squarylation of Bradykinin and CID-MS/MS Analysis Thereof

500 nmol of tert-butyl methylsquaric ester (2) in dioxane (50 μl) obtained in Example 1 was added in 50 nmol of bradykinin (4) in 200 μl of phosphate buffer (pH 8) and the resulting mixture was stirred for 2 days at a room temperature. Then, the reaction solution was purified with a high performance liquid chromatography (HPLC), resulting in bradykinin with squarylated N-terminal(5).

The resulting bradykinin with squarylated N-terminal (5) was subjected to CID-MS/MS analysis. Product ion peaks obtained from such an analysis are shown in a chart diagram of FIG. 2.

Figure 2:
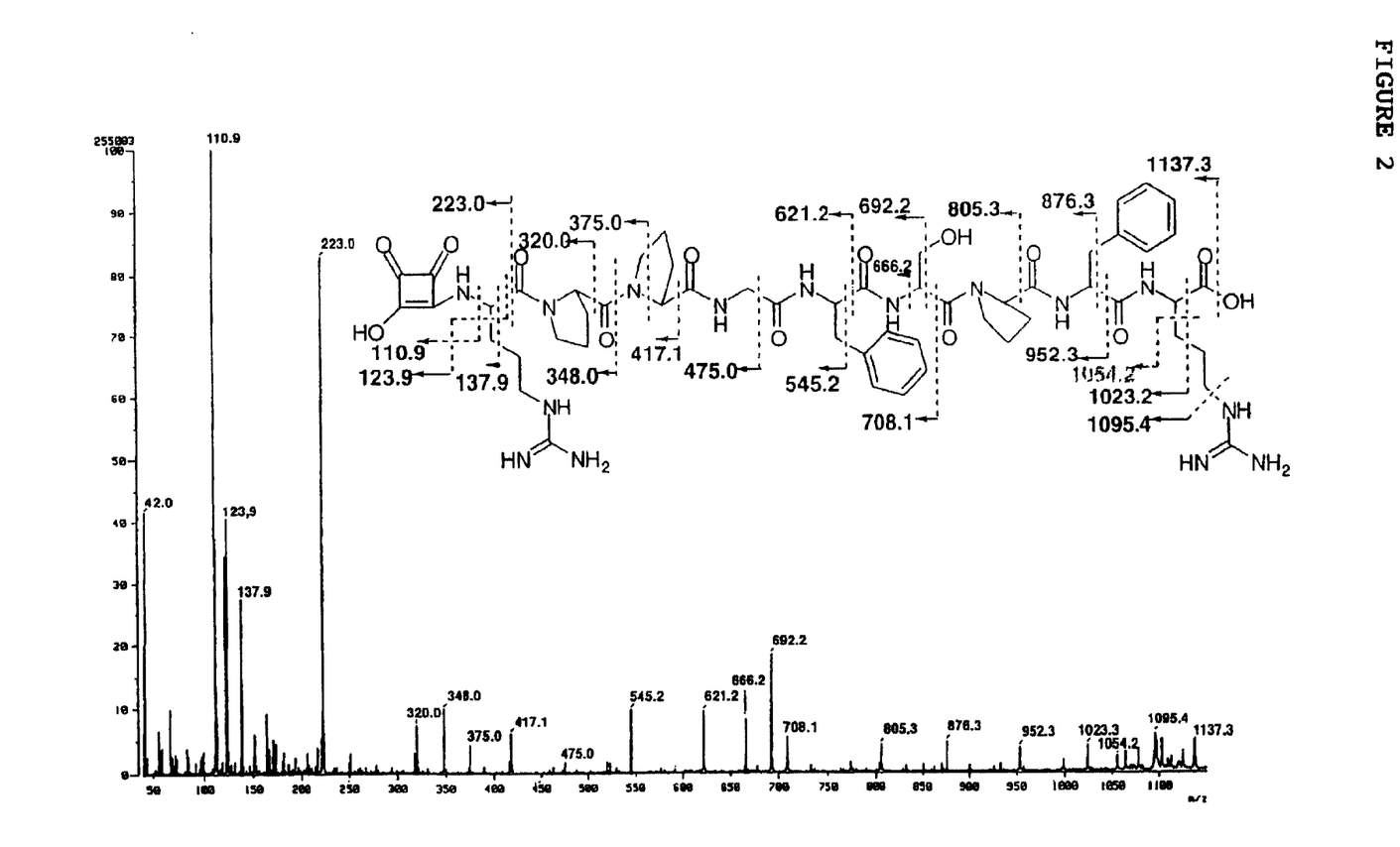
FIG. 2 is a CRF-chart diagram obtained by the CID-MS/MS analysis of squarylated brandykinin in Example 3.

As is evident from the chart diagram, the generation of regular CRF is observed.

Example 4

Squarylation of Enkephaline Analog and CID-MS/MS Analysis Thereof

A peptide (Gly-Gly-Phe-Leu) (6) was selected as an analog of enkephaline (Tyr-Gly-Gly-Phe-Leu) known as one of opioid peptides and was then subjected to squarylation and CID-MS/MS analysis.

206 mg of a compound (7) (0.548 mmol), which is a squaryl amino acid derivative represented by the formula (III) [$R^3$=i-Pr; $R^4$=Cbz (benzyloxycarbonyl)], and 132 mg of the above compound (6) (0.274 mmol) were dissolved in 5 ml of dichloromethane to obtain a reaction solution. Subsequently, 93 mg of 1-hydroxybenzotriazole (0.685 mmol), 303 mg of benzotriazole-1-yloxy-tris(dimethylamino)-phosphonium hexafluorophosphate (0.685 mmol), and 107 mg of diisopropylethylamine (0.822 mmol) were added in the reaction solution while stirring under ice-cooling. Then, the temperature of the reaction solution was elevated to a room temperature and was stirred for 12 hours. Then, the reaction solution was acidified by 1N hydrochloric acid aqueous solution, followed by extracting with ethyl acetate two times. An organic phase of the extract was washed with a saturated aqueous solution of sodium hydrogen carbonate and was then washed with brine, followed by drying with anhydrous magnesium sulfate. The solvent was removed by distillation under a reduced pressure and the residue was then subjected to a silica-gel column chromatography (ethyl acetate/hexane=1:1 to 1:0) for separation and purification. Consequently, a peptide (Gly-Gly-Phe-Leu (Bzl)) having a squaryl group on its N-terminal was obtained as 113 mg (49%) an oily product colored with pale yellow.

[à]$^{16}_D$: −2.5° (c=0.93, CHCl$_3$) HRMS (FAB): m/z (C$_{45}$H$_{54}$N$_5$O$_{11}$): Calculated value 840.3820 (M+H)$^+$; Measured value: 840.3820

Next, 33 mg (0.0393 mmol) of the peptide (Gly-Gly-Phe-Leu (Bzl)) having a squaryl group on its N-terminal obtained in the preceding step was added in a mixture (3 ml) of 30% hydrobromic acid and acetic acid, followed by stirring for 2 hours at a room temperature. Then, the reaction solution was subjected to distillation under a reduced pressure. The residue thus obtained was subjected to a column chromatography (water/methanol=2:1 to 1:1) using Cosmisil (registered trademark) to separate and purify the target compound (8) having a squaryl group on its N-terminal. Consequently, the target compound (8) was obtained as 13 mg (60%) of an oily product colored with pale yellow.

[à]$^{19}_D$: +23.5° (c=4.0. H$_2$O) HRMS (FAB): m/z (C$_{27}$H$_{36}$N$_5$O$_9$): Calculated value 574.2512 (M+H)$^+$; Measured value: 574.2514

Figure 3:
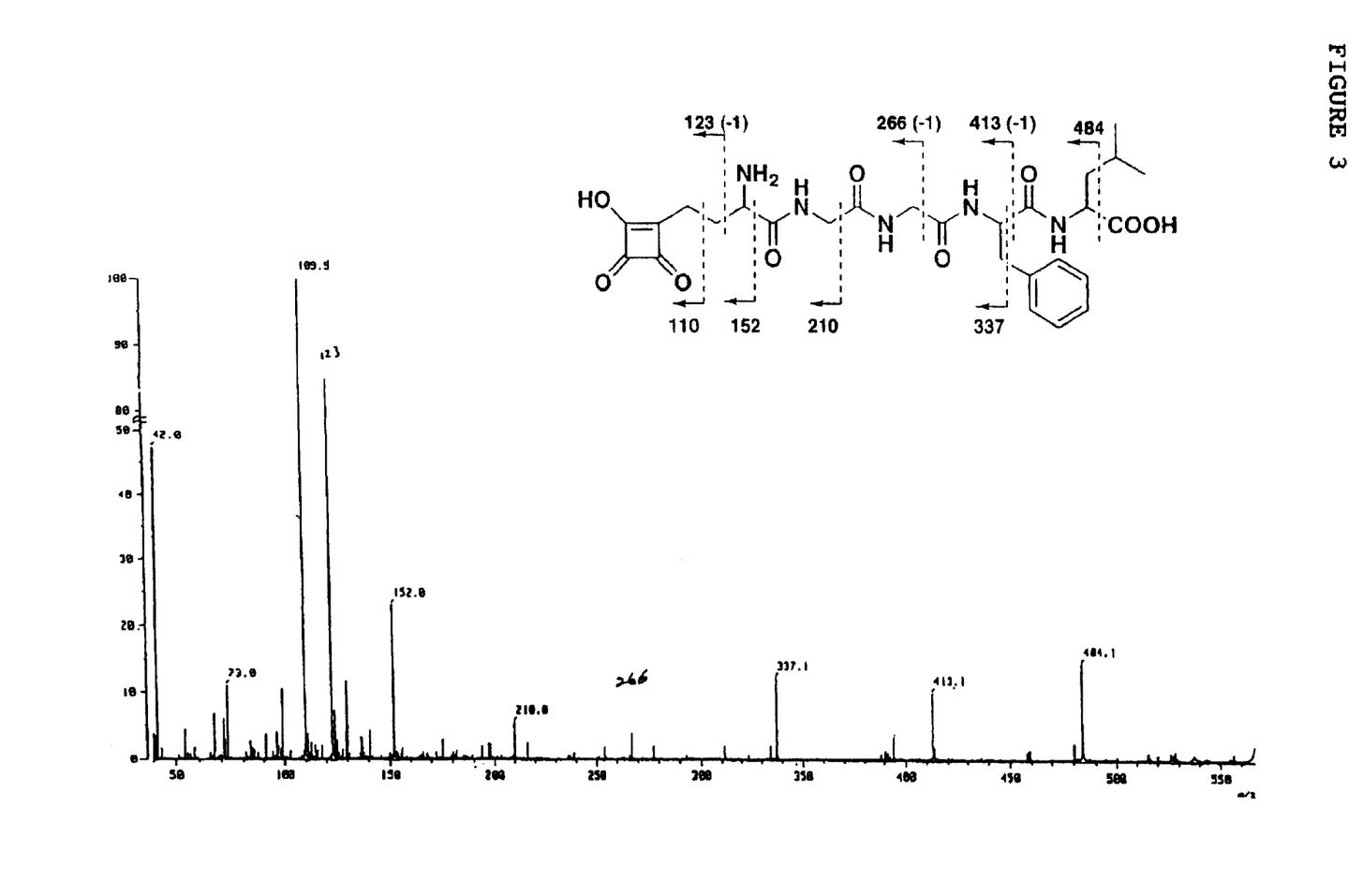
FIG. 3 is a CRF-chart diagram obtained by the CID-MS/MS analysis of squarylated enkepalin analog in Example 4.

The compound (8) having a squaryl group on its N-terminal thus obtained was subjected to CID-MS/MS analysis. The resulting product ion peaks are shown in a chart diagram in FIG. 3. As is evident from the results shown in the figure, it is found that regular CRF is generated on the chart of product ion peaks.

Example 5

Squarylation of Philanthotoxin Analogs and CID-MS/MS Analysis Thereof philanthotoxin

-continued spermine

Philanthotoxin (PhTX) is one of bee venom toxins and is a non-competitive blocker for glutamine acid receptors, having a polyamine structure. As an analog of such a toxin, spermine, one of bio-polyamines was selected and was then subjected to squarylation and CID-MS/MS analysis.

(a) Preparation of Squaryl Amino Acid Derivative (13)

100 mg of 10% palladium-carbon and 200 mg of acid anhydride (10) were added in a methanol solution of a known compound (9) (629 mg, 1.09 mmol). Then, the mixture was stirred for 1 hour under an atmosphere of hydrogen gas. Subsequently, the mixture was filtered to remove the catalyst. Filtrate was condensed under a reduced pressure and was then subjected to a silica-gel column chromatography (ethyl acetate/hexane=0:1 to 1:1) to separate and purify a target compound (11) from the mixture. Consequently, the target compound (11) was obtained as 533 mg (93%) of an oily product colored with pale yellow.

Next, 10 μl of 12 N HCl aqueous solution was added in a dichloromethane solution of the compound (11) while stirring under ice-cooling. Then, the temperature of the mixture was elevated to a room temperature, followed by stirring for 1.5 hours. After completing the reaction, the mixture was neutralized using a saturated aqueous solution of sodium hydrogen carbonate and was then extracted with ethyl acetate. An organic phase of the extract was washed with brine and was then dried with anhydrous magnesium sulfate. Then, the product was subjected to distillation to remove the solvent. Subsequently, the residue was subjected to a silica-gel column chromatography (ethyl acetate/hexane=0:1 to 1:1) to separate and purify a target compound (12) from the mixture. Consequently, the target compound (12) was obtained as 435 mg (92%) of an oily product colored with pale yellow.

A trifluoroacetic acid was added in a dichloromethane solution of the compound (12) obtained in the precedent step while stirring under ice-cooling. Then, the temperature of the mixture was elevated to a room temperature, followed by stirring for 1.5 hours. The reaction solution was condensed under a reduced pressure. The resulting condensate was dissolved in dichloromethane and triethylamine was then added in this solution while stirring. Subsequently, the reaction solution was condensed under a reduced pressure, resulting in a target compound (13) having the formula (III) ($R^3$=i-Pr; $R^4$=n-BuCO). The resulting compound (13) was directly supplied to the next step without purification.

(b) Squarylation of Spermine and CID-MS/MS Analysis Thereof

-continued (15)

The compound (13) obtained in the precedent step was dissolved in dichloromethane. Then, 1-hydroxybenzotriazole (205 mg, 1.52 mmol), benzotriazole-1-yloxy-tris(dimethylamino)phosphonium hexafluorophosphate (676 mg, 1.52 mmol), diisopropylethylamine (295 mg, 2.28 mmol), and the compound (14) (381 mg, 0.761 mmol) were successively added in the mixture while stirring under ice-cooling. Subsequently, the temperature of the reaction solution was elevated to a room temperature, followed by stirring for 20 hours. After completing the reaction, the reaction solution was subjected to the extraction using ethyl acetate. An organic phase of the resulting extract was successively washed with a saturated aqueous solution of sodium hydrogen carbonate, an aqueous solution of 1 N hydrochloric acid, and brine, followed by drying with anhydrous magnesium sulfate. The dried product was distilled under a reduced pressure to remove the solvent. The residue thus obtained was subjected to a silica-gel column chromatography (ethyl acetate/hexane=1:1 to 1:0) to separate and purify a target compound. Consequently, 453 mg (75%) of an oily product colored with pale yellow was obtained.

Next, the oily yellow product obtained in the precedent step was dissolved in 1 ml of acetone, followed by the addition of 1 ml of 1N hydrochloric acid aqueous solution. The mixture was stirred for 2 hours at a room temperature. Subsequently, the mixture was distilled to remove the solvent, resulting in 250 mg (96%) of a target compound (15) in which squaryl group was introduced.

Then, the obtained compound (15) was subjected to CID-MS/MS analysis. The resulting product ion peaks were shown in the chart diagram of FIG. 4.

Figure 4:
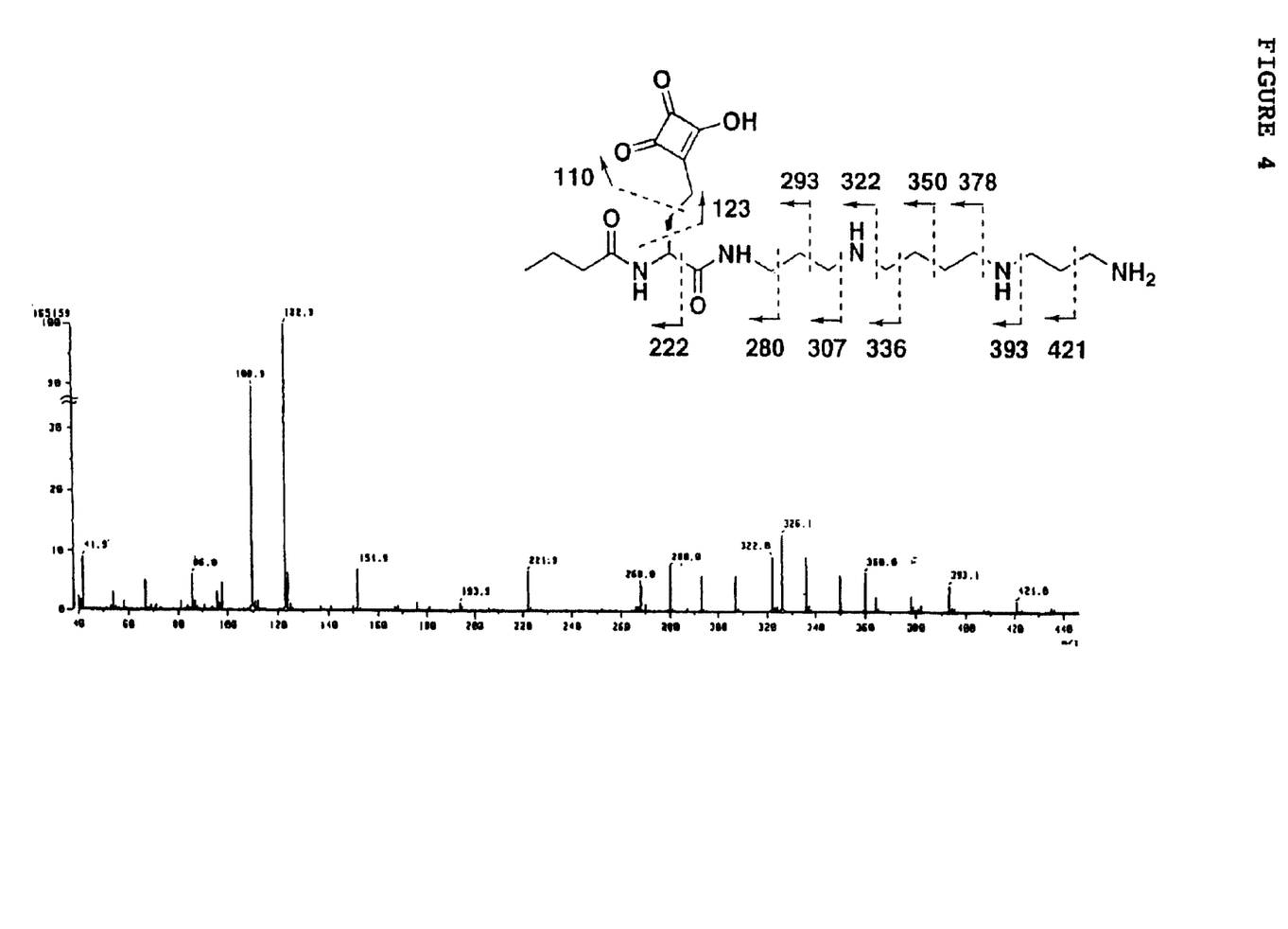
FIG. 4 is a CRF-chart diagram obtained by the CID-MS/MS analysis of squarylated philanthotoxin analog in Example 5.

As is evident from the chart diagram, the generation of regular CRF can be recognized. Especially in the case of spermine in the present example, there is a problem with respect to a distinction between sequences. That is, the problem of whether the polyamine methylene chain sequence is —$C_3$—$C_4$—$C_3$— or —$C_4$—$C_3$—$C_3$—. However, it turned out that the information about a primary structure for allowing the above distinction had been obtained.

Example 6

Edman Degradation and Squarylation of Mastparan, and CID-MS/MS Analysis Thereof (a) Edman Degradation A phenylisothiocyanate (17) solution (20 μl) was added in a mixture solution (200 μl) of ethanol:triethylamine:water=7:1:1 with 20 nmol of mastparan (16). Then, the mixture solution was heated at 50° C. for 10 minutes under a nitrogen gas flow. After completing the reaction, the reaction content was dried under a reduced pressure. Another mixture solution (400 μl) of heptane:ethyl acetate=10:1 with 100 il of water was added in that solution. Subsequently, the resulting mixture was stirred, followed by subjecting to centrifugal separation. After the centrifugation, the upper organic phase was decanted, whereas the lower water phase was collected. Then, the mixture solution (400 μl) of heptane:ethyl acetate=10:1 was added in the obtained water phase. The resulting mixture was stirred and was then subjected to centrifugal separation. After the centrifugation, the upper organic phase was decanted, whereas the lower water phase was collected. Then, the mixture solution (400 μl) of heptane:ethyl acetate=2:1 was added in the obtained water phase again. The resulting mixture was stirred and was then subjected to centrifugal separation. After the centrifugation, the upper organic phase was decanted, whereas the lower water phase was collected. The obtained water phase was dried under a reduced pressure, followed by the addition of 10 μl of trifluoroacetic acid. Then, the mixture was heated at 50° C. for 3 minutes under a nitrogen gas flow and was dried under a reduced pressure, resulting in an Edman-degradation product.

(b) Squarylation and CID-MS/MS Analysis

40 μl of phosphate buffer (pH 8) was directly added in the Edman-degradation product obtained in the precedent step, followed by the addition of tert-butyl, methylsquaric ester (2) (400 nmol) in dioxane 40 μl solution. The mixture was stirred for 2 days at a room temperature. After the heating, 20 μl of tryfluoroacetic acid was added in the mixture, followed by heating at 50° C. for 6 minutes. Subsequently, the mixture was dried under a reduced pressure, resulting in a product (18) as a compound in which isoleucine (Ile), an amino acid on the N-terminal of mastparan, was removed by the cleavage and an amino group of second asparagine (Asn) was squarylated.

The product (18) obtained in the precedent step was subjected to CID-MS/MS analysis. As a result, the generation of regular CRF was observed. However, it turned out that it was insufficient for structural analysis.

Example 7

New Edman Degradation and Squarylation of Fc-55, and CID-MS/MS Analysis Thereof (19)

(21)

(a) New Edman Degradation 800 nmol of di-Boc guanidinomethylphenyl isothiocyanate (20) in dioxane solution (1 μl) was added to a mixture solution (10 μl) of ethanol:triethylamine:water=7:1:1 with 10 nmol of Fc-55 (19) which is a peptide derived from Madagascar scorpion. Then, the mixture was heated at 50° C. for 5 minutes under a nitrogen gas flow. After completing the reaction, the reaction content was dried under a reduced pressure, followed by the addition of a mixture solution (200 μl) of heptane:ethyl acetate=10:1 with 20 μl of water. Subsequently, the mixture was stirred and was then subjected to centrifugal separation. After the centrifugation, the upper organic phase was decanted, whereas the lower water phase was collected. 200 μl of a mixture solution of heptane:ethyl acetate=10:1 was added in the obtained water phase. The mixture was stirred and was then subjected to centrifugal separation. The upper organic phase was decanted, whereas the lower water phase was collected. Furthermore, 200 μl of a mixture solution of heptane:ethyl acetate=2:1 was added in the obtained water phase. Subsequently, the mixture was stirred and was then subjected to centrifugal separation. After the centrifugation, the upper organic phase was decanted, whereas the lower water phase was collected. The obtained water phase was dried under a reduced pressure, followed by the addition of trifluoroacetic acid (10 μl). Subsequently, the mixture was heated at 50° C. for 3 minutes under a nitrogen gas flow and was then dried under a reduced pressure, resulting in an Edman-degradation product.

(b) Squarylation and CID-MS/MS Analysis

8 μl of phosphate buffer (pH 8) was added in the Edman-degradation product obtained in the precedent step, followed by the addition of tert-butyl, methylsquaric ester (2) in dioxane 2 μl solution. The mixture was stirred for 4 hours at a room temperature. After drying, a target product (21) was obtained as a compound in which isoleucine (Ile)(i.e., an amino acid on the N-terminal of FC-55) was removed by the cleavage and an amino group of second leucine (Leu) was squarylated.

The obtained compound (21) was subjected to CID-MS/MS analysis. From the results in the chart diagram of product ion peaks, the application of novel Edman decomposition method allowed the conversion of amino group on the side chain of lysine to p-guanidylmethyl pheylthiocarbamine form. Thus, the polarity of guanidylmethyl group on this para-position allowed the increase in ionization rate. Consequently, the generation of regular CRF was observed with greater clarity.

Just as in the case with the above compounds, other physiologically active peptides or the like were reacted with the reagent obtained in Example 1 of the present invention. Therefore, the corresponding compound having squarylated N-terminal were prepared. As a result of CID-MS/MS analysis, the generation of regular CRF was observed. By the way, the fragmentation was caused between $sp^3$ carbons. An amide bond having the property of $sp^2$ and the cleavage of aromatic group were substantially not observed.

Accordingly, the MS/MS analysis using charge-remote fragment (CRF) to be obtained by high-energy CID has an advantage of constant cleavage and fragmentation forms. Therefore, the information of a primary structure of a long-chain organic molecule can be provided with great precision. Also, the presence of a polar functional group of strong acidity or strong basicity on the end of the long-chain molecule is essential for the induction of CRF.

As is evident from the above description, the present invention confirmed the novel application of squaric acid diesters which can be used as raw materials for preparing drugs and optical materials and provided as a complex unit having both strong-acidity and aromaticity. That is, the squaric acid is used as reagent for structural analysis of a nitrogen-containing organic compound using the method of CID-MS/MS. From this time, therefore, the present invention will exert considerable power for the structural analysis of complex nitrogenous organic compounds.

According to the method of the present invention, a trace quantity of a sample, especially a sample in pico-order amounts, can be subjected to structural analysis. In this point, it is very difficult for the prior art technologies to elucidate chemical structures of physiologically active substances which occur naturally in nature because of their trace amounts. However, such a structural analysis can be attained by applying the method of the present invention. Therefore, the present invention gives an enormous amount of brightness on future studies of searching and synthesizing physiologically active substance.

What is claimed is:

1. A method for structural analysis of at least one nitrogen-containing organic chain compound using a high-energy collision induced dissociation-mass/mass spectrometry (CID-MS/MS spectrometry), comprising the steps of:

introducing a squaric acid residue into an N-terminal end of the at least one nitrogen-containing organic chain compound, where the squaric acid residue is represented by the chemical formula (I)

inducing charge-remote fragmentation (CRF) using a high-energy collision induced dissociation-mass/mass spectrometry (CID-MS/MS spectrometry); and measuring one or more properties of the fragmented compound, and correlating the measurement to the structure of the at least one nitrogen-containing organic chain compound, wherein the nitrogen-containing organic chain compound is selected from the group consisting of peptides, peptide esters, polyamines, polyamine ethers, and organic chain compounds having amino groups on their ends.

2. The method according to claim 1, further comprising providing a squaric acid derivative represented by the chemical formula (II):

wherein each of $R^1$ and $R^2$ similarly or differently represents a hydrogen atom, a lower alkyl group, an alkenyl group, aryl group, or an aralkyl group, said squaric acid derivative being provided to introduce said squaric acid residue into the N-terminal end of the at least one nitrogen-containing organic chain compound.

3. The method according to claim 1, further comprising providing a squaryl amino acid derivative represented by the chemical formula (III):

(III)

wherein $R^3$ represents a hydrogen atom, a lower alkyl group, an alkenyl group, an aryl group, or an aralkyl group, $R^4$ represents a protecting group for an amino group, and n represents a positive integer 1 or 2, said squaryl amino acid derivative being provided to introduce said squaric acid residue into the N-terminal end of the at least one nitrogen-containing organic chain compound.

* * * * *